United States Patent
Häberlein et al.

(10) Patent No.: US 7,435,558 B2
(45) Date of Patent: Oct. 14, 2008

(54) ASCERTAINING THE PATIENT RELATED RISK OF CARIES

(75) Inventors: Ingo Häberlein, Weilheim i. Obb. (DE); Ingo Wagner, Wörthsee (DE); Rainer Guggenberger, Herrsching (DE); Thomas Bökenkamp, Germering (DE); Christian Steinbeiss, München (DE); Michaela Bader-Danziger, Kaufering (DE)

(73) Assignee: 3M ESPE AG, Seefeld (DE)

( * ) Notice: Subject to any disclaimer, the term of this patent is extended or adjusted under 35 U.S.C. 154(b) by 499 days.

(21) Appl. No.: 10/468,958

(22) PCT Filed: Feb. 22, 2002

(86) PCT No.: PCT/EP02/01907

§ 371 (c)(1),
(2), (4) Date: Mar. 11, 2004

(87) PCT Pub. No.: WO02/068679

PCT Pub. Date: Sep. 6, 2002

(65) Prior Publication Data

US 2004/0141960 A1 Jul. 22, 2004

(30) Foreign Application Priority Data

Feb. 23, 2001 (DE) .................................. 101 08 900

(51) Int. Cl.
*C12Q 1/26* (2006.01)

(52) U.S. Cl. ...................................................... 435/25

(58) Field of Classification Search ................... 435/25, 435/7.1; 424/49, 50
See application file for complete search history.

(56) References Cited

U.S. PATENT DOCUMENTS

| | | | |
|---|---|---|---|
| 3,332,743 A | 7/1967 | Green |
| 4,133,875 A | 1/1979 | Hillman |
| 4,254,222 A | 3/1981 | Owen |
| 4,324,860 A | 4/1982 | Hillman |
| 4,351,899 A | 9/1982 | Owen |
| 4,582,795 A | 4/1986 | Shibuya et al. |
| 6,105,761 A | 8/2000 | Peuker et al. |
| 6,428,972 B2 | 8/2002 | Jacobson et al. |
| 2001/0036636 A1 | 11/2001 | Jacobson et al. |
| 2004/0029171 A1 * | 2/2004 | Wagner et al. ............... 435/7.1 |

FOREIGN PATENT DOCUMENTS

| | | |
|---|---|---|
| DE | 297 14 246 U1 | 12/1998 |
| DE | 199 26 728 A1 | 12/2000 |
| DE | 101 08 900 A1 | 9/2002 |
| EP | 0 097 904 B1 | 10/1986 |
| EP | 0 895 943 A2 | 2/1999 |
| EP | 0 895 943 A3 | 2/1999 |
| EP | 0 895 943 B1 | 4/2001 |
| EP | PCT/EP0107778 * | 1/2002 |
| JP | 11-507228 T | 6/1999 |
| WO | WO 01/12237 A1 | 2/2001 |

OTHER PUBLICATIONS

Abbe et al, Oxygen and the sugar metabolism in oral streptococci, Proc. Finn. Den., Soc., 1991, vol. 87, p. 477-487.*
A. M. Aass et al., "Microbiologic tests in epidemiologic studies: are they reproducible?" *Scand J. Dent Res.*, vol. 102, pp. 355-360 (1994).
M. M. Coogan et al., "Salivary and plaque acids in caries active and caries free subjects," *Journal of the Dental Association of South Africa*, vol. 51, pp. 823-827 (Dec. 1996).
C. Dawes et al., "A Theoretical Analysis of the Effects of Plaque Thickness and Initial Salivary Sucrose Concentration on Diffusion of Sucrose into Dental Plaque and its Conversion to Acid During Salivary Clearance," *Journal Dental Research*, vol. 65, pp. 89-94 (Feb. 1986).
J. L. Kelsay et al., "Pyruvate and lactate in human blood and saliva in response to different carbohydrates," *J. Nutr.*, vol. 102(5), pp. 661-666 (1972) (English Language Abstract Only (1 pg)).
Kleinfelder and Kirchner "Die diagnostische Sicherheit biologischer Speicheltests zur Bestimmung des individuellen Kariesrisiko" ["The diagnostic reliability of biological saliva tests for determination of the individual risk of caries"], *Dtsch. Zahnärztliche Zeitschrift 48*, pp. 646-648 (1993) (English Language Summary on p. 647) (English Language Translation attached (3 pgs)).
S. Kneist et al., "Handelsübliche Speicheltests zum Mutans-Nachweis—Übersicht und Effizienzbewertung," *Quintessenz 50*, 33-43 (1999) (English Language Translation attached (10 pgs)).

(Continued)

*Primary Examiner*—Jon P Weber
*Assistant Examiner*—Tiffany M Gough
(74) *Attorney, Agent, or Firm*—Mueting, Raasch & Gebhardt, P.A.

(57) ABSTRACT

The invention relates to a method for the determination of the patient-related risk of caries by determination of lactic acid and/or lactate in saliva and to a method for the location-specific determination of the patient-related risk of caries.

7 Claims, No Drawings

OTHER PUBLICATIONS

Lura et al., "Acid formation in saliva and plaque and its relation to caries activity," *Duetsche Zahn-, Mund-und Kieferheilkunde*, vol. 28, H. 11, u 12, pp. 447-455 (1958) (English Language Abstract included (1 pg.)).

G. E. Minah et al., "Metabolic Differences Between Saliva From Caries-Active and Caries- And Restoration-Free Children," *Archivs Oral Biol.*, vol. 31, No. 10, 633-638 (1986).

K. Oba et al., "Partial Purification and Characterization of L-Lactate Dehydrogenase Isozymes from Sweet Potato Roots," *J. Biochem.*, vol. 81, pp. 1193-1201 (1977).

M. Perez et al., "Determination of the Maximum Steady State of Lactate (MLSS) in Saliva: An Alternative to Blood Lactate Determination," *Japanese Journal of Physiology*, vol. 49 (4), pp. 395-400. (Aug. 1999) (Abstract included).

S. Rupf et al., "Quantitative determination of *Streptococcus mutans* by using competitive polymerase chain reaction," *Eur. J. Oral. Sci.*, vol. 107, 75-81 (1999).

G. Sornin et al., "Study on lactate dehydrogenase and its isoenzymes in total human saliva," *Spectra 2000* (Deux Mille) vol. 109, Suppl. 27-29. (1986) (English Language Abstract only (1 pg.)).

R. A. Williams et al., "Purification of the fructose 1,6-bisphosphate-dependent lactate dehydrogenase from *Streptococcus uberis* and an investigation of its existence in difference forms," *Biochem. J.*, vol. 236, 721-727 (1986).

W.A. Wood (Ed.), "Automated Enzymatic Determination of L(+)- and D(-)- Lactic Acid," *Methods in Enzymology*, vol. 89, Carbohydrate Metabolism Part D, Academic Press, Inc., Cover page and pp. 29-35 (1982).

Iwami, "Influence of Environment on Glycolysis in Streptococci," *Kitasato Arch. of Exp. Med.*, 1988;61(1):1-20.

Iwami, "Glycolysis of Oral Streptococci," *Tohoku Univ. Dent. J.*, 2003;22:79-98. English language translation included.

Nishijima, "Enzymological Properties of Lactate Dehydrogenase from *Streptococcus mitior*,"*Nihon University Dentistry Journal*, 1990;64:24-31. English language translation included.

Tamura et al., "Carbohydrate Metabolism of Dental Plaque," *Nihon University Dentistry Journal*, 1988;62:477-481. English language translation included.

Tanaka, "Specific Activities of Lactate Dehydrogenase in Dental Plaque Collected from Carious Lesion and Normal Portion of Deciduous Dentition," *Nihon University Dentistry Journal*, 1986;60:487-493. English language translation included.

Yamada, "Sugar Metabolism - in vitro and in vivo by Microorganisms in Dental Plaque," *Biochemistry*, 2001;73(4):239-246. English language translation included.

International Preliminary Examination Report for PCT/EP2002/001907 (7 pgs.).

* cited by examiner

ASCERTAINING THE PATIENT RELATED RISK OF CARIES

The present application is a U.S. National Stage Application of PCT/EP02/01907, filed 22 Feb. 2002. The application also claims the benefit under 35 U.S.C. §119 of foreign application no. DE 101 08 900.7, filed 23 Feb. 2001.

The invention relates to a test which is suitable for ascertaining the patient-related risk of caries by determination of lactic acid and/or lactate.

PRIOR ART

Caries is an infectious disease. The causative organisms most frequently mentioned include *Streptococcus* spp. and *lactobacilli*. Caries-causing micro-organisms have in common, amongst other things, that they take up and ferment sugars, for example sugars from the diet, and excrete acids as metabolic end products.

A distinction must be made, as a matter of principle, between microbial acid release in the saliva and the release of acid in dental plaque, because the carious lesions of teeth are caused a priori by the acid formed by micro-organisms that adhere to tooth surfaces, also referred to hereinafter as plaque. Local acidification of the environment at the tooth surfaces causes the hydroxyapatite to dissolve and consequently is the chemical cause of the formation of caries lesions.

The rapidity with which plaque may be acidified and how strongly acidified it may become depends, inter alia, on the buffering capacity of the saliva, on the buffering capacity of the plaque liquid, on the microbial growth (Coogan, M. M., Motlekar, H. B. Journal of the Dental Association of South Africa 51, 823-827 (1996)) and on diffusion processes (Dawes, C., Dibdin, G. H. Journal Dental Research 65, 89-94 (1986)) in the plaque.

This complex interplay of physiological, microbiological and chemical factors gives rise to the caries potential in plaque. These factors are present in degrees that differ from one patient to another.

One of the aims of modern dentistry is to assign patients to risk groups. Early recognition of the risk of caries, before the occurrence of caries lesions, is beneficial.

It has not been possible for determination of the patient-related risk of caries by means of plaque analysis to become established in practice because, to reach a diagnosis, a large number of individual samples would have to be taken and analysed. Such tests are laborious and too expensive and their management is too complex.

As an alternative to plaque testing, ascertaining the patient-related risk of caries is attempted by testing saliva. It is accordingly presumed that the quantifiable amounts of *Streptococcus mutans* and/or *lactobacilli* in the saliva correlate with the amounts of *Streptococcus mutans* and/or *lactobacilli* in the plaque and that it is possible, as a result, to deduce the risk of caries to a patient using a saliva test.

Various methods are available for the determination of caries-causing micro-organisms, for example *Streptococcus mutans* and/or *lactobacilli*, in saliva.

1. The determination of caries-causing micro-organisms is usually carried out after incubation of the samples for several days in suitable culture media, because the number of micro-organisms originally present is not sufficient to obtain a result directly. After multiplication of the micro-organisms over a period lasting from hours to days, the colony-forming units (CFU's) are counted and the number of micro-organisms present in the sample is deduced (Kneist, S.; Klein, C.; Rupf, S.; Eschrich, K. Quintessenz (1999) 50, 33-43).

It is disadvantageous that the correlation between the number of carious micro-organisms in the saliva and the risk of caries is no more than unsatisfactory, because it is not the number of micro-organisms but rather their metabolic activity that is crucial. Moreover, incubation of the samples results in the establishment of a culture of pathogenic micro-organisms, which has to be treated with the appropriate cautionary measures in order to minimise risks in the practice. Special disposal is necessary. In addition to those disadvantages, the incubation methods required to reach a microbiological diagnosis are expensive and very time-consuming.

2. Immunological methods are a further approach to the determination of caries-causing micro-organisms in saliva. In this case, monoclonal or polyclonal antibodies against surface structures of the micro-organisms being determined are employed.

Compared to the incubation methods according to section 1, these immunological methods are more specific, faster and cheaper, but have clear failings in terms of reproducibility (Kneist, S.; Klein, C.; Rupf, S.; Eschrich, K. Quintessenz (1999) 50, 33-43). For example, saliva contains not only viable micro-organisms but also considerable quantities of micro-organisms that have died. The ratio between dead and viable micro-organisms may differ from one patient to another. The fact that the antibodies are unable to distinguish between viable micro-organisms and dead micro-organisms means that there is an unpredictable range of variation when deducing the existing pathogenic potential of the micro-organisms evaluated (Aass, A. M.; Preus, H. R., Zambon, J. J., Gjermo, P. Scand J. Dent Res (1994) 102, 355-360). Furthermore, the reservation that the correlation between the number of carious micro-organisms in the saliva and the risk of caries is no more than unsatisfactory, because it is not the number of micro-organisms but rather their metabolic activity that is crucial, also holds true in this case.

3. The method having the highest sensitivity is based on polymerase chain reaction (PCR) technology. Minute quantities of micro-organisms can be detected with a high degree of specificity. The PCR technology is time-consuming, complex, costly and not easily mastered (Rupf, S., Kneist, S., Merte, K., Eschrich, K. Eur. J. Oral. Sci. (1999) 107, 75-81). In this case too, the reservation that a distinction is not made between living and dead micro-organisms must also be made. Furthermore, the additional reservation that the correlation between the number of carious micro-organisms in the saliva and the risk of caries is no more than unsatisfactory, because it is not the number of micro-organisms but rather their metabolic activity that is crucial, also holds true in this case.

All methods for the quantification of caries-causing micro-organisms in the saliva in order to ascertain the risk of caries have the crucial disadvantage that it is not possible to reach the desired finding—the patient-related risk of caries—because it is not possible to deduce, from the amounts of caries-causing micro-organisms present in the saliva, the caries potential thereof in plaque.

Because the composition of saliva is different from one patient to another and has an effect on the metabolic capacity of the micro-organisms present (Minah, G. E., McEnery, M. C., Flores, J. A. Archivs Oral Biol. (1986) 31, 633-638), it is recommended that, in addition to the quantification of caries-causing micro-organisms, the acidification of the patient's saliva that can be caused by sugars should also be investigated. The reduction in pH is due to microbial acid release and is seen as a measure of the metabolic activity of the micro-organisms in the saliva. The observed reduction in pH value in the saliva is, however, dependent upon the level of the buffering capacity of a patient's saliva. It is accordingly recommended that, in order to the determine the patient-related risk of caries, the buffering capacity of the saliva should also be combined with the quantification of caries-causing micro-organisms and pH measurement in the saliva.

Clinical experience shows, however, that even the combination of quantification of Streptococcus mutans/lactobacilli, pH determination and buffering capacity cannot provide a reliable finding with respect to the patient-related risk of caries (Kleinfelder and Kirchner "Die diagnostische Sicherheit biologischer Speicheltests zur Bestimmung des individuellen Kariesrisiko" ["The diagnostic reliability of biological saliva tests for determination of the individual risk of caries"], Dtsch. Zahnärztliche Zeitschrift (1993) 48, 646-648).

The specifications U.S. Pat. No. 3,332,743 and EP-A-0 097 904 describe a further attempt at deducing the patient-related risk of caries from the metabolic activity of micro-organisms in the saliva. The capacity of saliva to reduce resazurin to resorufin is observed, the metabolic activity of the micro-organisms being said to correlate with the rate of formation of resorufin. The patient-related risk of caries is deduced from the rate at which resorufin is formed. The reduction of resazurin to resorufin is brought about by microbial dehydrogenases. It is not only *Streptococcus mutans* and *lactobacilli* which have dehydrogenases that are capable of reducing resazurin to resorufin. For that reason, the resazurin/resorufin test is used in general as a test for the viability of micro-organisms and is accordingly not specific for the caries pathogens which contribute, via acid release, to acidification of the oral environment and it cannot, therefore, be used for ascertaining the patient-related risk of caries.

A further possibility, discussed in the literature, for ascertaining the metabolic activity of caries-causing micro-organisms which damages the hard substance of teeth is the release of acids, for example formic acid, acetic acid, propionic acid and lactic acid. Which acids are crucially involved in damaging the hard substance of teeth is dependent on, for example, the supply of nutrients. If sufficient glucose is present, streptococci secrete lactic acid preferentially whereas, when the availability of glucose is limited, acetic acid, propionic acid and formic acid are formed preferentially.

The patent specifications U.S. Pat. No. 4,351,899 and U.S. Pat. No. 4,254,222 describe a method for the enzymatic determination of lactic acid in biological fluids, especially blood. As a result of enzymatic reduction of lactic acid by a dehydrogenase there is formed, besides pyruvate, nicotinamide adenine dinucleotide (NADH). NADH is subsequently determined using redox indicators, preferably tetrazolium derivatives and phenazine derivatives. Transferring this process to saliva would make possible a rapid and simple method for the determination of the metabolic activity of cariogenic micro-organisms and, consequently, of the risk of caries. The process described in those specifications cannot, however, be used in the case of saliva because a subsidiary reaction which occurs in the saliva crucially falsifies the signal generated by the redox indicators. Even without addition of the dehydrogenase required for the detection reaction, the redox indicators are reduced by saliva components in combination with NAD and signals are produced which are not attributable to the presence of lactate in the saliva.

Problem

The problem of the present invention is accordingly to provide a method which makes possible evaluation of the prevailing patient-related risk of caries and, in the process, avoids the known disadvantages of the prior art.

Solution

It has been found, surprisingly, that patients having an increased risk of caries can be identified by the test used in the context of the method according to the invention.

The combination of this test with diagnostic dental impressions, for example those according to DE-A-199 26 728, is also in accordance with the invention. By that means it is possible to distinguish between those patients who, despite the fact they show a caries risk in the saliva or on the tongue, do not have plaque on their teeth that carries a risk of caries and those who do have an actual risk.

The advantage of the invention lies, moreover, in the fact that it is possible for the risk of caries in a patient to be clearly ascertained, leading to identification of appropriately directed medication, and for over- and under-treatment to be avoided.

The advantage of the invention lies, furthermore, in the fact that, using the saliva test, it is possible to establish the need for further investigations, for example a diagnostic dental impression, and indeed at the start of treatment, for example in the context of group prophylaxis in schools and kindergartens. It is also advantageous that the course of treatment can be simply monitored.

The expression "risk of caries" is to be understood in the context of the invention as being both the patient's basic risk of suffering from caries and also the risk that is dependent upon the time of day and eating habits. For the purpose of determining the basic risk, which is governed by the fundamental composition of the oral flora, the patient advantageously carries out simple cleaning measures such as, for example, rinsing and/or teeth-cleaning, preferably teeth-cleaning, before the method according to the invention is used. When determining the risk that is dependent upon the time of day and eating habits, the cleaning measure need not be carried out necessarily but in a preferred embodiment of the method according to the invention should nevertheless be performed.

The expressions "comprising" and "containing" in the context of this specification introduce a non-exhaustive listing.

The saliva test used in accordance with the invention is based on the surprising effect that, subject to the meeting of appropriate precautionary conditions, the formation of lactic acid is outstandingly suitable as a measure of the metabolic activity of micro-organisms in the saliva for the determination of the prevailing patient-related risk of caries and can be ascertained by quantification or semi-quantification of the lactic acid.

In the context of the present invention, the expression "lactate" is to be understood as L(+)-lactate, and the expression lactate dehydrogenase (LDH) is to be understood as L(+)-lactate dehydrogenase.

For detection of the lactic acid, it can, in principle, be involved in chemical, biochemical or physical reactions in which detectable signals are generated.

It has been found, surprisingly, that the undesirable subsidiary reaction between redox inhibitors and saliva components can be suppressed by maintaining specific ratios, in terms of amounts, between lactate dehydrogenase, saliva and an inhibitor, namely pyruvate. The reason that this finding is surprising is that pyruvate is a known inhibitor of lactate dehydrogenase (see, for example, Williams, R. A., Andrews, P., Biochem. J. 236, 721-727 (1986); Oba, K., Mura Kami, S., Uritani, I., J. Biochem. 1193-1201 (1977)). For the person skilled in the art it is an unforeseeable solution that, contrary to the technical teaching, the measurement enzyme—in this case lactate dehydrogenase—must be used in the presence of a known inhibitor in order to be able to suppress the unspecific subsidiary reaction of the saliva to an extent such that an enzymatic determination of the lactic acid by means of lactate dehydrogenase and redox inhibitors is possible. The expression pyruvate is to be understood here as being pyruvic acid or its salts, especially its Na or K salt.

For the enzymatic determination of lactic acid in saliva by means of lactate dehydrogenase—which can be obtained, for example, from bacteria, preferably lactobacilli, streptococci or staphylococci, from animals, preferably pigs, bovine animals, chickens or rabbits, from plants, or from human tissue, for example placenta—suitable ratios, in terms of amounts, between the saliva and lactate dehydrogenase must be maintained. Per 0.1 ml of saliva there should be used between 0.001 and 100 units of lactate dehydrogenase, preferably between 0.01 and 10 units of lactate dehydrogenase and very preferably between 0.05 and 1 unit of lactate dehydrogenase.

In addition, pyruvate should be used in concentrations between 0.001 µmol and 5 µmol per 0.1 ml of saliva, preferably between 0.01 µmol and 2.5 µmol per 0.1 ml of saliva and very preferably between 0.01 µmol and 1 µmol per 0.1 ml of saliva.

1 unit of lactate dehydrogenase is to be understood as referring to the conversion of 1 µmol of pyruvate per minute and mg of protein.

By way of example, redox indicators from the following group can be used in accordance with the invention: methylene blue, 5-cyano-2,3-ditolyl-tetrazolium chloride (CTC), 2-(4-iodophenyl)-3-(4-nitrophenyl)-5-phenyl-2H-tetrazolium chloride (INT), 8-dimethylamino-2,3-benzophenoxazine (Meldola's blue), 1-methoxy-phenazine methosulphate (MPMS) 5-(3-carboxymethoxyphenyl)-2-(4,5-dimethylthiazolyl)-3-(4-sulphophenyl)-tetrazolium (MTS), 3-(4,5-dimethylthiazol-2-yl)-2,5-diphenyltetrazolium bromide (MTT), 3,3'-(3,3'-dimethoxy-4,4'-biphenylene)-bis[2-(4-nitrophenyl-5-phenyl)]-2H chloride (NBT), nitro-tetrazolium violet (NTV), phenazine methosulphate (PMS), sodium 3'-[1-[(phenylamino)carbonyl]-3,4-tetrazolium]bis(4-methoxy-6-nitro)-benzenesulphonic acid (XTT), phenazine ethosulphate (PES, WST-1).

Preference is given among those to Meldola's blue, PES, PMS, MTS, MTT and XTT; special preference is given to PES, PMS, MTS and MTT.

The concentrations of the redox indicators in the test mixture are between 0.001 and 10 mmol/l, preferably between 0.01 and 5 mmol/l, and very preferably between 0.05 and 2 mmol/l.

Depending upon requirements, the redox indicators can be used in the test in solid form, for example in powder, granule or tablet form.

In accordance with the invention, NAD is preferably used in non-limiting, but also in non-inhibiting, amounts, for example in concentrations between 0.01 and 10 mmol/l, preferably between 0.05 and 5 mmol/l, and very preferably between 0.1 and 1 mmol/l, based on the entire test mixture.

Depending upon requirements, NAD can be used in the test in solid form, for example in powder, granule or tablet form.

Lactate dehydrogenases from bacteria, animals and plants have pH optima between 4.0 and 10.0. Depending upon the lactate dehydrogenase used, suitable buffer solutions having different pH values must be used. Suitable buffer substances are especially members of the following groups:

phosphates, for example sodium phosphates, sodium hydrogen phosphate, sodium dihydrogen phosphate, potassium phosphate, potassium hydrogen phosphate, potassium dihydrogen phosphate, pyrophosphate;

carbonates, for example sodium carbonate, potassium carbonate, sodium hydrogen carbonate, potassium hydrogen carbonate;

acetic acid/acetate; citric acid/citrate, diethylbarbituric acid, tris(hydroxymethyl)-aminomethane (TRIS), glycine, glycylglycine (Glygly), N-(2-acetamido)-2-amino-ethanesulphonic acid (ACES), N-(2-acetamido) iminodiacetate (ADA), N,N-bis(2-hydroxyethyl)-2-aminoethanesulphonic acid (BES), N,N-bis(2-hydroxyethyl)glycine (BICINE), 2,2-bis(hydroxyethyl) iminotris(hydroxymethyl)methane (BIS-TRIS), 2-cyclohexylamino)ethanesulphonic acid (CHES), 2-[4-(2-hydroxyethyl-1-piperazine)]ethanesulphonic acid (HEPES), 3-[4-(2-hydroxyethyl-1-piperazinyl)]-propanesulphonic acid (HEPPS), 2-morpholinoethanesulphonic acid (MES), 3-morpholinopropanesulphonic acid (MOPS), piperazine-1,4-bis(2-ethanesulphonic acid) (PIPES), N-[tris(hydroxymethyl)-methyl]-2-aminoethanesulphonic acid (TES), N-tris(hydroxymethyl)-methyl]-glycine (TRICINE).

Special preference is given to phosphate buffers, Tris buffer, Glygly buffer and acetic acid/acetate buffer.

Depending upon the detection reaction, a pH value between 1 and 12 may be required. The concentrations of the buffer solutions may, depending upon requirements, be between 0.001 mol/l and 5.0 mol/l, preferably between 0.01 mol/l and 1.0 mol/l, very preferably between 0.1 mol/l and 0.5 mol/l.

Adjustment of the pH of the reaction solution can also be achieved by using in the test, depending upon requirements, defined amounts of buffer substances in solid form, for example in powder or tablet form. Should it be necessary, buffer substances may also be used in the test in liquid form.

Buffer substances, redox indicators, NAD and lactate dehydrogenase and other production adjuvants may be added as combinations in solid form or as a combination in solid and liquid form, for example as a powder in a range between 1 mg and 20 g, preferably between 10 mg and 10 g, more preferably between 50 mg and 5 g and very preferably between 100 mg and 1 g, or in tablet form, for example between 1 and 20 tablets, preferably between 2 and 10 tablets, very preferably between 3 and 5 tablets. The weight of the tablets may be, for example, between 1 mg and 2 g, preferably between 10 mg and 1.5 g, and very preferably between 100 mg and 1 g.

Production adjuvants are to be understood as being, for example, adjuvants that are known from galenical chemistry, for example dextrans, sugars, aluminium oxide, glasses, quartzes, cellulose derivatives, waxes, fats and salts.

Buffer substances, redox indicators, NAD and lactate dehydrogenase can also be added to the saliva sample in liquid form, in which case they can either be added directly if they are liquids or dissolved beforehand in solvents such as water, ethanol or propanol. Volumes of between 0.001 ml and 20 ml, preferably between 0.01 and 10 ml and very preferaby between 0.1 ml and 1 ml, can be used.

The formation of the lactic acid and of the detectable signal can be detected in a continuous process proceeding in parallel, in which case, for example, after a defined time interval of between 0.01 min and 60 min, preferably between 0.1 min and 30 min, very preferably between 1 min and 10 min, the detectable signal is evaluated or the formation of the metabolite to be detected and/or of the detectable signal is terminated.

For the purpose of termination there come into consideration, for example, stopping reagents such as inhibitors, for example phosphate, or a sudden change in pH, for example initiated by hydrochloric acid or sodium hydroxide solution, or the addition of proteases or surfactants.

The formation of the lactic acid can also be carried out in an independent incubation step, in which case, for example after a defined time interval of between 0.01 min and 60 min, preferably between 0.1 min and 30 min, very preferably between 1 min and 10 min, the formation of the lactic acid is terminated.

For the purpose of termination there come into consideration, for example, stopping reagents, as described above, or heating of the sample to temperatures between 50 and 100° C., or a combination of a stopping reagent and temperature increase.

For the purpose of terminating the formation of lactic acid by the micro-organisms, a very great variety of methods may be used, for example

- irradiation with high-energy light, such as UV
- radioactive treatment
- heat treatment
- pH change, for example by addition of acids or bases
- addition of surfactants
- addition of inhibitors, such as heavy metal salts, alkylating agents
- addition of micro-organism-destroying substances, such as lysozyme, triclosan, chlorhexidine, taurolidine
- removal of the micro-organisms from the saliva sample being investigated, for example by ultra-filtration, micro-filtration using sterile filters or centrifugation or a suitable combination of two or more of those methods.

For the purpose of carrying out the test according to the invention, for example between 0.001 ml and 20 ml, preferably between 0.01 ml and 10 ml, very preferably between 0.1 ml and 1 ml, of saliva is transferred to a reaction vessel. In general, the amount of saliva used must be at least sufficiently large for a detectable signal to be obtained for the lactate determination as a result of signal-producing additives.

It can also be advantageous to transfer micro-organisms from regions of the oral cavity into the saliva by mechanical action and then to transfer the saliva sample into a reaction vessel. For example, coating on the tongue can be released therefrom using a suitable implement, such as a tongue spatula or scraper, and the sample taken only thereafter.

It is also possible to take, instead of a direct saliva sample, a sample of micro-organisms from a suitable location in the oral cavity by means of suitable sampling devices and to subject that sample, instead of the saliva, to the basic method according to the invention. In this case, preference is given to removal of coating on the tongue from an area of tongue of from 0.01 to 25 $cm^2$, preferably from 0.1 to 10 $cm^2$ and very preferably between 1 and 5 $cm^2$, by means of cotton-wool tips, swabs or other absorbent materials and devices. In general, the tongue coating must be taken from an area of tongue that is at least sufficiently large for a detectable signal to be obtained for the lactate determination as a result of signal-producing additives.

It can be advantageous, for the purpose of standardisation of the detectable signal in the patient-related patient saliva, for substances to be added to the saliva which make possible the maximum possible lactic acid formation, for example sugars, preferably sucrose and glucose. These substances can be introduced either in solid or liquid form or in a combination of solid and liquid form.

It is possible, for example, for the mouth to be rinsed with a sugar solution, such as an aqueous solution of, for example, glucose, fructose, galactose, sucrose and maltose having a content of between 0.1 and 70% sugar, preferably between 1 and 50% sugar, and very preferably between 5 and 30% sugar, before sampling of the saliva or removal of the tongue coating.

It can likewise be advantageous for sugars, such as glucose, fructose, galactose, sucrose, maltose, up to saturation between 0.1 and 70%, preferably 1 and 60%, and very preferably 10 and 50% to be added to the saliva sample itself.

It can also be advantageous for between 0.1 and 10 g, preferably between 0.5 and 5 g, and very preferably between 1 and 2 g, of sugar in the form of, for example, a sugar cube, powdered sugar or sugar tablet to be allowed to dissolve in the oral cavity before sampling of the saliva and removal of the tongue coating.

It can be advantageous, for the purpose of removing the tongue coating by means of cotton-wool tips, swabs or other absorbent materials, to soak the latter with a solution containing between 0.1 and 70% sugar, preferably between 1 and 50% sugar, and very preferably between 5 and 30% sugar, and to use them after drying.

In a likewise preferred embodiment of the method according to the invention, the cotton-wool tips, swabs or other absorbent materials used, for example, for removal of the tongue coating can comprise one or more diagnostic constituents such as, for example, sucrose, NAD, MTP, PMS, LDH or pyruvate, as they are described hereinbefore. Preference is given, inter alia, to NAD being present therein.

In an especially preferred embodiment, the cotton-wool tips, swabs or other absorbent materials used, for example, for removal of the tongue coating comprise both at least one sugar solution as described above and at least one diagnostic constituent such as, for example, NAD.

The invention can in practice be made available, for example, in the form of a blister pack, as is described, for example, in DE 297 142 46 U. This mode of presentation allows the methods according to the invention to be carried out in especially simple manner.

The present invention relates also to a method for the location-specific determination of the patient-related risk of caries using a diagnostic impression compound.

In this case, the patient-related risk of caries is first determined by means of the method according to the invention described above and, in the event of a positive risk, an impression is taken of at least one jaw region, for example of the upper and/or lower jaw, using a diagnostic impression compound.

Suitable diagnostic impression compounds are, for example, those from DE-A-199 26 728, especially alginate-, polyether-, silicone- or polyether-silicone-based compounds. Such compounds are hardenable or film-forming carrier materials containing diagnostically useful additives for location- and substance-specific intraoral diagnosis in a preferred amount of from 0.0001 to 10% by weight. Suitable diagnostic additives are, according to that specification, dye indicators, antibodies, enzymes and any other substance familiar to the skilled person acquainted with the development of diagnostic test systems.

Such impression compounds exhibit, in the fully hardened impression material, a detectable signal—for example a coloration—at those locations where an increased risk of caries is present. For that purpose, metabolites of the caries-promoting micro-organisms are selectively used as the active species in the detection method employed.

In this context it is possible to use, for example, a pre-formulated diagnostic impression compound. It is, however, likewise possible to use a conventional impression compound, which the person carrying out treatment can convert into an impression compound having a diagnostic function by adding diagnostically effective substances.

The invention will be described below in greater detail by means of Examples; the invention is not to be limited thereby.

EXAMPLES

Application Example 1

For mixing the signal-producing solution, there are transferred to a plastic test tube (2.5 ml) having a screw closure, using a pipette, 0.1 ml of NAD solution (stock solution 30 mmol/l NAD in Glygly buffer 50 mmol/l, pH 9.0), 0.1 ml of MTT (stock solution 1.5 mmol/l MTT in Glygly buffer 50 mmol/l, pH 9.0), 0.1 ml of PMS solution (stock solution 1.0 mmol/l PMS in Glygly buffer 50 mmol/l, pH 9.0), 0.1 ml of LDH solution (stock soluton lactate dehydrogenase (LDH) 60 units/ml in Glygly buffer 50 mmol/l, pH 9.0) and 0.1 ml of pyruvate solution (stock solution pyruvate 25 mmol/l in Glygly buffer 50 mmol/l, pH 9.0), the screw lid is closed and shaking is carried out for 5 sec.

The patient collects saliva from the mouth and transfers at least 1 ml of saliva into a 5 ml plastic test tube having a screw closure. Using a pipette, 0.6 ml is transferred into a reaction vessel already containing 0.25 g of sucrose. The reaction vessel is closed by means of the screw lid and shaken for 5 sec.

After 3 min, the signal-producing solution is added to the saliva sample in the reaction vessel. The closed reaction vessel is shaken for 5 sec. After 3 min, 0.4 ml of acetic acid solution (stock solution acetic acid 1 mol/l in water) is added to the reaction vessel in order to terminate the formation of the detectable signal. The course of the reaction can be followed by the colour change from yellow to blue. Yellow indicates no risk of caries, and the more intense the blue colour, the higher the risk of caries.

At a wavelength of incident light of 570 nm, an extinction ΔE/min of 0.957 was measured with a UVIKON 930 spectrphotometer using a plastic cell having a volume of 1 ml.

Comparison Example 1a

Comparison Example 1a was performed as Application Example 1, but no pyruvate was added. An extinction of 3.3 was measured.

Comparison Example 1b

Comparison Example 1b was performed as Application Example 1, but neither pyruvate nor LDH were added. An extinction of 0.815 was measured.

Comparison Example 1c

Comparison Example 1c was performed as Application Example 1, but no LDH was added. An extinction of 0.156 was measured.

The Comparison Examples 1a to 1c, together with Application Example 1, show that, even though pyruvate does inhibit the LDH (compare 1a), the inhibition by pyruvate is over-compensated by increased addition of LDH (compare 1b) and nevertheless one or more unknown subsidiary reactions are suppressed (compare 1c).

Application Example 2

For mixing the signal-producing solution, there are transferred to a plastic test tube (2.5 ml) having a screw closure, using a pipette, 0.1 ml of NAD solution (stock solution 3 mmol/l NAD in Glygly buffer 50 mmol/l, pH 9.0), 0.1 ml of MTT (stock solution 0.15 mmol/l MTT in Glygly buffer 50 mmol/l, pH 9.0), 0.1 ml of PMS solution (stock solution 0.1 mmol/l PMS in Glygly buffer 50 mmol/l, pH 9.0), 0.1 ml of LDH solution (stock soluton lactate dehydrogenase (LDH) 40 units/ml in Glygly buffer 50 mmol/l, pH 9.0), 0.1 ml of pyruvate solution (stock solution pyruvate 2.5 mmol/l in Glygly buffer 50 mmol/l, pH 9.0), the screw lid is closed and shaking is carried out for 5 sec.

Using a pipette, 100 µl are pipetted onto an absorbent swab 2 cm×0.6 cm×0.78 mm and freeze-dried. The dried swab is stuck surface-to-surface onto one end of a polyester strip (7 cm×0.6 cm×0.25 mm). A saliva sample, as described under Application Example 1, paragraph 2, has been previously prepared in a reaction vessel. The swab on the test strip is introduced into the saliva sample completely. After 3 min, the test strip swab is immersed in a vessel containing 2 ml of stopping reagent consisting of 50 mmol/l sodium hydrogen phosphate solution having a pH of 7.5. The greater the intensity of the blue coloration of the swab on the test strip, the higher the risk of caries.

Application Example 3

A signal-producing solution is prepared as described in Application Example 2, paragraph 1. The patient allows a sugar cube to dissolve in the mouth and collects saliva from the mouth. A cotton-wool tip (for example, Q-Tip) is introduced into the mouth and left there for 5 sec in order to soak up saliva. The saliva-soaked cotton-wool region of the tip is immersed in the signal-producing solution and left there for 3 min. The blue coloration produced on the cotton-wool region of the cotton-wool tip is then evaluated. The more intense the blue coloration, the higher the risk of caries.

Application Example 4

A test strip is prepared as described in Application Example 2, from paragraph 1. The patient allows a sugar cube to dissolve in the mouth. The test strip is introduced into the mouth and the absorbent swab is placed on the middle of the tongue and rubbed in order to pick up coating from the tongue. The absorbent swab of the test strip is immersed in the signal-producing solution and left there for 3 min. The blue coloration produced on the swab is then evaluated. The more intense the blue coloration, the higher the risk of caries.

Application Example 5

The ingredients, as described in Application Examples 1 to 4, for carrying out the saliva test are contained in this kit. 20 g of alginate (Palgat, from ESPE) are contained in a bag for the diagnostic impression. The alginate is transferred to a mixing bowl (250 ml). A signal-producing solution prepared according to DE-A-199 26 728 and containing 0.26 g of glycylglycine, 0.24 g of tri(hydroxymethyl)aminomethane, 36 mg of NAD, 0.9 mg of phenazine methosulphate, 3 mg of 3-(4,5-dimethylthiazolyl-2)-2,5-diphenyltetrazolium bromide (MTT) and 1850 units of lactate dehydrogenase, by means of which the release of lactic acid by caries-causing micro-organisms in plaque can be observed, is held ready in a vessel. The signal-producing solution is added to the alginate. Without delay, the mixture is mixed with a hand spatula until homogeneous (about 30 sec). Whilst the impression compound is being prepared, the patient allows a sugar cube to dissolve in the mouth. The impression compound is introduced into an impression tray. For taking the impression, the impression tray is pressed against either the upper jaw or the lower jaw and is left there for 3 min. The impression is removed from the mouth. The locations on the teeth that carry metabolically active, caries-causing micro-organisms are shown by blue dots and areas on the impression compound. The more intense the blue coloration, the higher the local risk of caries. The caries risk determined by the saliva test can be compared to the caries risk present on the teeth.

Application Example 6

A blister in accordance with DE 29714246 U is used. A cotton-wool tip (e.g. Q-Tip) is impregnated with a 50% by weight sugar solution. The cotton-wool tip is introduced into the mouth and rubbed and rotated on the middle of the tongue in order to take up coating from the tongue. The cotton-wool tip is introduced into the first reservoir of the blister. By pressing on the second reservoir, the signal-producing solution, prepared according to Application Example 2, paragraph 1, is passed into the first reservoir. By rotating the cotton-wool tip, the region having the saliva sample is wetted with the signal-producing solution. The cotton-wool tip can be removed from the blister after 3 min.

Comparison Example 1

Comparison Examples 1 and 2 were prepared in order to show that the teachings of the patent specifications U.S. Pat. No. 4,351,899 and U.S. Pat. No. 4,254,222 are not suitable for determining the patient-related risk of caries.

In accordance with the teaching of the patent specifications U.S. Pat. No. 4,351,899 and U.S. Pat. No. 4,254,222, 0.1 ml of Glygly buffer solution pH 9.0 containing 0.6 µmol of lactate, 0.6 µmol of NAD, 0.03 µmol of MTT, 0.02 µmol of PMS and 0.6 unit of lactate dehydrogenase were added to 100 µl of saliva and thoroughly mixed. At 570 nm, the course of the reaction was followed using a microplate reader (from Molecular Device). An increase in extinction of 0.6/min was measured. In the control experiment without saliva, a change in extinction of 1.1/min was measured. Result: saliva inhibits the enzyme lactate dehydrogenase required for signal production by 45%.

Comparison Example 2

In accordance with the teaching of the patent specifications U.S. Pat. No. 4,351,899 and U.S. Pat. No. 4,254,222, 0.1 ml of Glygly buffer solution pH 9.0 containing 0.6 µmol of lactate, 0.6 µmol of NAD, 0.03 µmol of MTT and 0.02 µmol of PMS were added to 100 µl of saliva and thoroughly mixed. At 570 nm, the course of the reaction was followed using a microplate reader (from Molecular Device). Even without the presence of lactate dehydrogenase, an increase in extinction of 0.4/min was measured. In the comparison experiment in the presence of 0.3 unit of lactate dehydrogenase, a change in extinction of 1.2/min was measured. Result: saliva contains components that are themselves able to reduce the redox indicators PMS/MTT and consequently falsify the measurement signal by 50%.

The invention claimed is:

1. A method for the determination of the patient-related risk of caries by determination of lactic acid and/or lactate in samples from the oral cavity, wherein, in case of saliva having a sample volume of 0.1 ml, between 0.001 and 100 Units of lactate dehydrogenase are added and pyruvate is added in concentrations of between 0.001 µmol and 5 µmol per 0.1 ml of sample volume and, in the case of biofilms which have been obtained from an oral cavity surface of 0.01 to 25 cm$^2$, between 0.001 and 100 Units of lactate dehydrogenase are added, and wherein in both cases NAD is present in a concentration between 0.001 and 10 mmol/l based on the entire test mixture and subsequently the resulting amount of NADH is measured, wherein the resulting amount of NADH detected is used to calculate the amount of lactic acid and/or lactate in the saliva or biofilm to determine the patient-related risk of caries.

2. A method according to claim 1, wherein the sample volume is removed only after transfer of micro-organisms into the saliva by mechanical action on at least one region of the oral cavity.

3. A method according to claim 2, wherein the region of the oral cavity is the tongue.

4. A method according to claim 1, wherein, before carrying out sampling, there is added to the saliva a substance which induces or increases the, formation of lactic acid and/or lactate.

5. A method according to claim 4, wherein, before carrying out the detection method, at least one buffer solution is added.

6. A method according to claim 1 wherein after removal of the sample volume from the oral cavity, pyruvate is added to the sample.

7. A method for the location-specific determination of the patient-related risk of caries, wherein the method comprises: determining the patient-related risk of caries by determination of lactic acid and/or lactate in a sample from the oral cavity, wherein, in case of saliva having a sample volume of 0.1 ml, between 0.001 and 100 Units of lactate dehydrogenase are added and pyruvate is added in concentrations of between 0.001 µmol and 5 µmol per 0.1 ml of sample volume and, in the case of biofilms which have been obtained from an oral cavity surface of 0.01 to 25 cm$^2$, between 0.001 and 100 Units of lactate dehydrogenase are added, and wherein in both cases NAD is present in a concentration between 0.001 and 10 mmol/l based on the entire test mixture and subsequently the resulting amount of NADH is measured, wherein the resulting amount of NADH detected is used to calculate the amount of lactic acid and/or lactate in the saliva or biofilm to determine the patient-related risk of caries; and subsequently making an impression of at least one jaw region using a diagnostic impression compound comprising a film-forming carrier material and a diagnostic substance, wherein the diagnostic substance produces an observable signal in the presence of lactic acid released by caries-causing microorganisms.

* * * * *

UNITED STATES PATENT AND TRADEMARK OFFICE
CERTIFICATE OF CORRECTION

PATENT NO. : 7,435,558 B2
APPLICATION NO. : 10/468958
DATED : October 14, 2008
INVENTOR(S) : Ingo R. Haeberlein It is certified that error appears in the above-identified patent and that said Letters Patent is hereby corrected as shown below:

Column 1,
Line 1 (Title), Delete "Patient Related" and insert -- Patient-Related --, therefor.

Column 2,
Line 66, Delete "Archivs" and insert -- Archives --, therefor.

Column 6,
Line 58, Delete "preferaby" and insert -- preferably --, therefor.

Column 9,
Line 21, Delete "soluton" and insert -- solution --, therefor.
Line 41-42, Delete "spectrphotometer" and insert -- spectrophotometer --, therefor.

Column 10,
Line 57, Delete "palgat" and insert -- palghat --, therefor.

Column 12,
Line 30, In Claim 4, after "the" delete ",".
Line 34, In Claim 6, after "1" insert -- , --.
Line 34, In Claim 6, after "wherein" insert -- , --.

Signed and Sealed this

Nineteenth Day of May, 2009

JOHN DOLL
*Acting Director of the United States Patent and Trademark Office*

UNITED STATES PATENT AND TRADEMARK OFFICE
CERTIFICATE OF CORRECTION

PATENT NO. : 7,435,558 B2  Page 1 of 1
APPLICATION NO. : 10/468958
DATED : October 14, 2008
INVENTOR(S) : Ingo R. Haeberlein It is certified that error appears in the above-identified patent and that said Letters Patent is hereby corrected as shown below:

<u>Title Page, Item [54] and Column 1, line 1,</u>
(Title), Delete "Patient Related" and insert -- Patient-Related --, therefor.

<u>Column 2,</u>
Line 66, Delete "Archivs" and insert -- Archives --, therefor.

<u>Column 6,</u>
Line 58, Delete "preferaby" and insert -- preferably --, therefor.

<u>Column 9,</u>
Line 21, Delete "soluton" and insert -- solution --, therefor.
Line 41-42, Delete "spectrphotometer" and insert -- spectrophotometer --, therefor.

<u>Column 10,</u>
Line 57, Delete "palgat" and insert -- palghat --, therefor.

<u>Column 12,</u>
Line 30, In Claim 4, after "the" delete ",".
Line 34, In Claim 6, after "1" insert -- , --.
Line 34, In Claim 6, after "wherein" insert -- , --.

This certificate supersedes the Certificate of Correction issued May 19, 2009.

Signed and Sealed this

Ninth Day of June, 2009

JOHN DOLL
*Acting Director of the United States Patent and Trademark Office*

UNITED STATES PATENT AND TRADEMARK OFFICE
CERTIFICATE OF CORRECTION

PATENT NO.         : 7,435,558 B2
APPLICATION NO. : 10/468958
DATED                 : October 14, 2008
INVENTOR(S)        : Ingo R. Haeberlein It is certified that error appears in the above-identified patent and that said Letters Patent is hereby corrected as shown below:

Title Page 2,
Line 6, Delete "Archivs" and insert -- Archives --, therefor.

Column 5,
Line 41, After "2H" insert -- tetrazolium --, therefor.

Signed and Sealed this

Twenty-first Day of July, 2009

JOHN DOLL
*Acting Director of the United States Patent and Trademark Office*